(12) United States Patent
Izzo et al.

(10) Patent No.: US 8,628,667 B2
(45) Date of Patent: Jan. 14, 2014

(54) CHROMATOGRAPHIC COLUMN AND METHODS FOR CONTROLLING SORBENT DENSITY

(75) Inventors: Gary Izzo, Norton, MA (US); Raymond P. Fisk, Norton, MA (US); Jonathan Belanger, Whitinsville, MA (US); Donald E. Ziniti, Cumberland, RI (US)

(73) Assignee: Waters Technologies Corporation, Milford, MA (US)

( * ) Notice: Subject to any disclaimer, the term of this patent is extended or adjusted under 35 U.S.C. 154(b) by 1508 days.

(21) Appl. No.: 11/941,160

(22) Filed: Nov. 16, 2007

(65) Prior Publication Data

US 2008/0110814 A1    May 15, 2008

Related U.S. Application Data

(60) Division of application No. 11/072,907, filed on Mar. 4, 2005, now Pat. No. 7,399,410, which is a continuation of application No. PCT/US03/28098, filed on Sep. 8, 2003.

(60) Provisional application No. 60/409,600, filed on Sep. 10, 2002.

(51) Int. Cl.
   *B01D 15/08* (2006.01)
(52) U.S. Cl.
   USPC ........................................ 210/656; 210/198.2
(58) Field of Classification Search
   USPC .............. 210/635, 656, 659, 198.2, 238, 282, 210/450, 456; 96/101, 106, 107
   See application file for complete search history.

(56) References Cited

U.S. PATENT DOCUMENTS

| | | | |
|---|---|---|---|
| 4,551,249 A | | 11/1985 | Shackelford et al. |
| 4,655,917 A | | 4/1987 | Shackelford et al. |
| 4,670,141 A | | 6/1987 | Shackelford et al. |
| 4,797,209 A | * | 1/1989 | Jackson ........................ 210/656 |
| 5,021,162 A | * | 6/1991 | Sakamoto et al. ............. 210/635 |
| 5,192,433 A | | 3/1993 | Shalon |
| 5,227,059 A | | 7/1993 | Shepherd |
| 5,462,659 A | * | 10/1995 | Saxena et al. ............... 210/198.2 |
| 5,525,303 A | | 6/1996 | Ford et al. |
| 5,582,723 A | | 12/1996 | Boone et al. |

(Continued)

FOREIGN PATENT DOCUMENTS

| | | |
|---|---|---|
| DE | 4118785 | 12/1992 |
| EP | 1306668 | 5/2003 |

(Continued)

OTHER PUBLICATIONS

"Performance of an 18-MM I.D. Column for Analytical and Semi-Pre-Preparative-Scale . . . ";Journal of Chrom, 122 (1976) 317-329.

(Continued)

*Primary Examiner* — Ernest G Therkorn
(74) *Attorney, Agent, or Firm* — Waters Technologies Corporation

(57) ABSTRACT

Disclosed herein are apparatus and methods for mitigating column bed compression over time. This invention provides for an improved column design and method of controlling bed density in a chromatographic column using a protruding portion of a filter assembly. The invention results in a higher sorbent bed density than can normally be achieved using a fixed length column of conventional design. The invention may be implemented as a unique filter assembly or as a column tailored for the application and a matching filter assembly.

4 Claims, 7 Drawing Sheets

(56) References Cited

U.S. PATENT DOCUMENTS

| | | |
|---|---|---|
| 5,596,876 A | 1/1997 | Manura et al. |
| 5,601,708 A | 2/1997 | Leavesley et al. |
| 5,610,322 A | 3/1997 | Unger et al. |
| 5,693,223 A | 12/1997 | Yamada et al. |
| 5,730,943 A | 3/1998 | Ford et al. |
| 5,893,971 A | 4/1999 | Shalon et al. |
| 5,911,954 A | 6/1999 | Ford et al. |
| 5,951,873 A | 9/1999 | Shalon et al. |
| 5,997,742 A | 12/1999 | Gjerde et al. |
| 6,030,527 A | 2/2000 | Gjerde et al. |
| 6,117,329 A * | 9/2000 | Hargro .................. 210/656 |
| 6,132,605 A * | 10/2000 | Leavesley et al. ......... 210/198.2 |
| 6,139,732 A | 10/2000 | Pelletier |
| 6,139,733 A | 10/2000 | Hargro et al. |
| 6,162,362 A * | 12/2000 | Ma et al. ................ 210/656 |
| 6,221,252 B1 | 4/2001 | Hargro et al. |
| 6,294,087 B1 | 9/2001 | Hargro et al. |
| 6,436,284 B1 | 8/2002 | Leavesley et al. |
| 6,458,273 B1 | 10/2002 | Krakover et al. |
| 6,491,821 B2 | 12/2002 | Gjerde et al. |

FOREIGN PATENT DOCUMENTS

| | | |
|---|---|---|
| JP | 3007905 B | 5/1983 |
| JP | 63-032368 | 2/1988 |
| JP | 03-197862 | 8/1991 |
| JP | 07-198701 | 8/1995 |
| JP | 08-094604 | 4/1996 |
| JP | 08155207 | 6/1996 |
| JP | 09-511830 | 9/1997 |
| JP | 11-044681 | 2/1999 |
| JP | 11-174036 | 2/1999 |
| WO | 9527547 | 10/1995 |
| WO | WO 2004/024285 | 3/2004 |

OTHER PUBLICATIONS

Translation of Notice of Rejection for Japanese Patent Application No. 2004-536152, dated May 31, 2011.

* cited by examiner

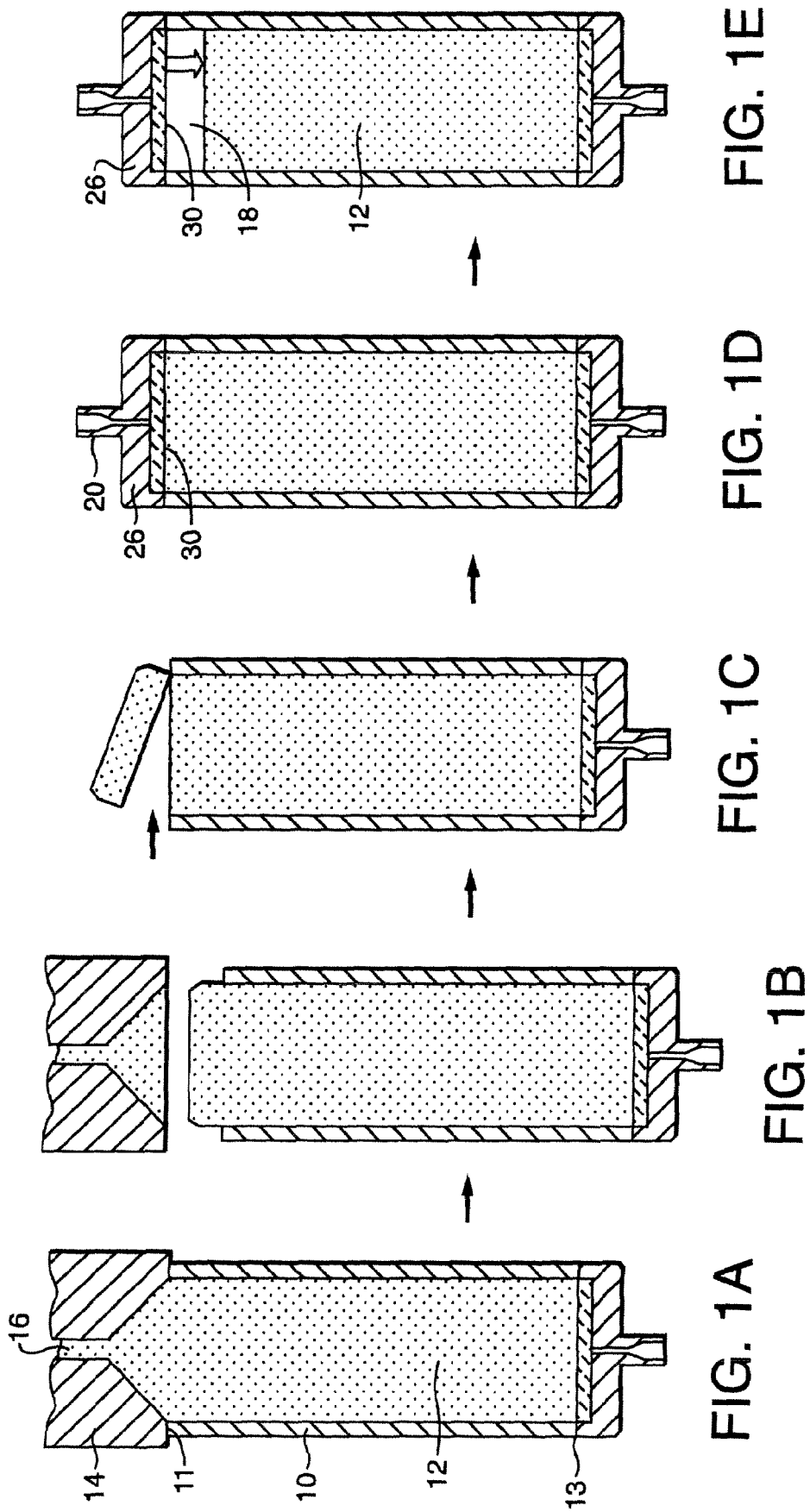

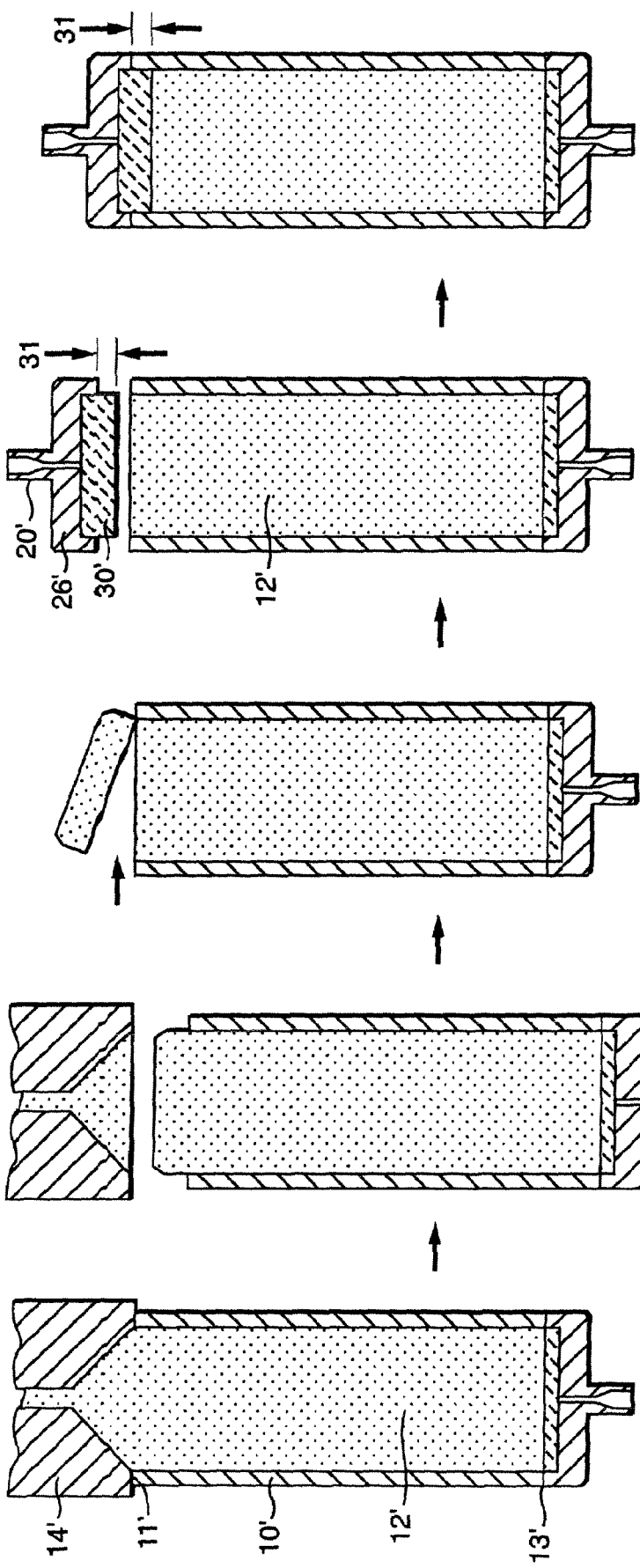

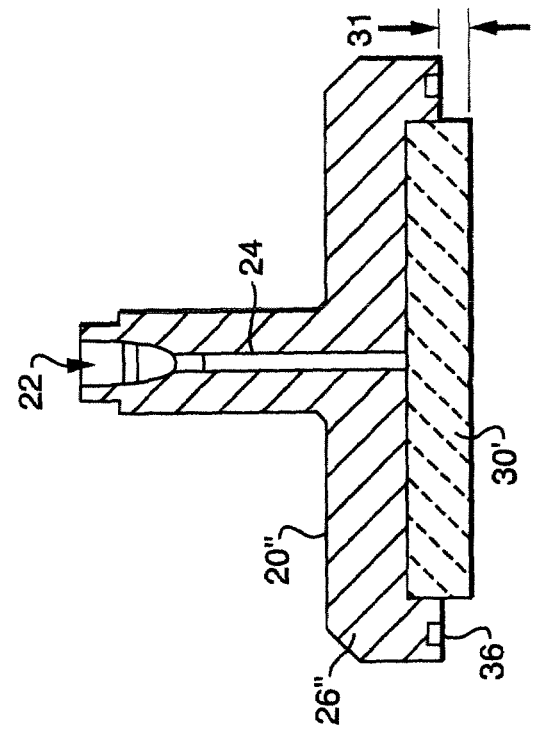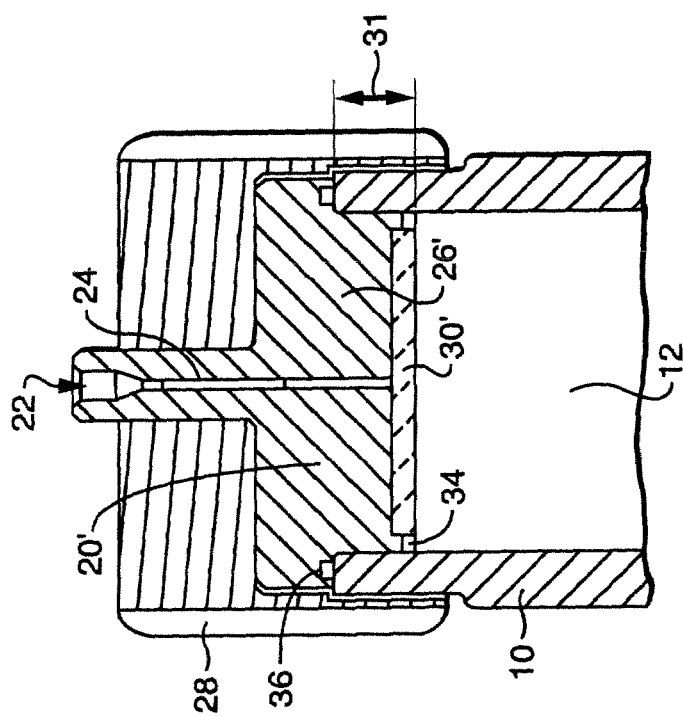

CHROMATOGRAPHIC COLUMN AND METHODS FOR CONTROLLING SORBENT DENSITY

CROSS REFERENCE TO RELATED APPLICATIONS

This application is a division of U.S. Ser. No. 11/072,907, filed Mar. 4, 2005 which application claims the benefit of and is a continuation of International Application No. PCT/US03/28098, filed Sep. 8, 2003 and designating the United States, which claims benefit of and priority to U.S. Provisional Application No. 60/409,600 filed Sep. 10, 2002. The entire contents of these applications are incorporated herein by reference.

FIELD OF INVENTION

The present invention relates to chromatography columns, in particular, to apparatus and methods for achieving high sorbent density within said columns.

BACKGROUND OF THE INVENTION

A common method used to separate analytes within a sample is liquid chromatography. Liquid chromatography employs specific chromatographic columns and one or more mobile phases used to both equilibrate the column and elute analytes therefrom. Chromatography columns are used to effectuate the separation, purification and study of analytes contained within a homogeneous or heterogeneous sample. Columns are packed with sorbent material (also referred to as the "stationary phase" or "packing bed") that provides a chemical milieu with which analytes of a sample can interact. Generally, the sorbent material contains functional groups having a specific chemistry. For example, reverse-phase columns have a stationary phase comprising molecules with one or more hydrophobic groups. These hydrophobic groups, e.g., a $C_{18}$ hydrocarbon chain, will interact with other molecules via hydrophobic interaction. This hydrophobic interaction can be interrupted with an organic mobile phase, thus eluting analytes from the stationary phase.

The most commonly used chromatographic columns, referred to herein as "conventional columns", are comprised of a column tube into which sorbent is packed, and inlet and outlet end fittings, which facilitate connection to the fluid stream, and which also contain filters that are designed to contain the sorbent bed within the column tube itself. These filters are disposed at each end face of the column tube.

In operation, the sorbent bed within the chromatographic column is subjected to fluid forces resulting from the flow of mobile phase through the column. Over time, these forces may disrupt the packing bed of the column resulting in voids or dead volume ($V_o$) within the column's packing bed. These voids have a detrimental effect on the performance of a column. Voids can in effect serve as mixing chambers within the confines of the column leading to the loss of column efficiency. For example, the practitioner may observe excessive peak tailing over time using a standard analyte, such peak tailing is indicative of a poor column.

An issue that plagues practitioners of chromatography is how to mitigate this loss of column performance. Some chromatography columns in the prior art employ a movable device situated within the column. This movable device, for example a piston, is designed to adjust the internal volume of the chromatographic column in response to changes in the sorbent bed density during use, thereby attempting to minimize the void volume within the column. However, these designs are typically very complex requiring multiple components and seals and are therefore inherently more expensive to produce. Additionally, the columns with these movable devices require that the column tube itself be significantly larger and therefore much less convenient to use. Further, these columns with movable devices do not contain a fixed volume of sorbent, which can lead to difficulty in predicting analyte retention times and the scaling of chromatographic methods across different column sizes Thus, there currently exists a need for a chromatography column that minimizes the effects of sorbent bed compression, which incorporates a simple, cost effective design, is highly portable and convenient to use, and does not negatively affect the column's chromatographic behavior. The present invention addresses this need in toto. In addition, the present invention provides for a method of increasing the sorbent bed density within a chromatographic column beyond what is possible with conventional fixed length column designs, thereby improving the stability of the column during use.

SUMMARY OF THE INVENTION

The present invention pertains to both apparatus and methods for minimizing column bed compression over time. This invention provides for an improved column design and method for controlling bed density in a chromatographic column using a protruding filter assembly. The columns and methods described herein produce a higher sorbent bed density than can normally be achieved using a fixed length column of conventional design.

The columns of the present invention comprise a column tube with a first and a second end, an inlet filter assembly affixed to the first column tube end, and an outlet filter assembly affixed to the second column tube end. The column tube, together with the inlet and outlet filter assemblies, defines an interior chamber that serves as a receptacle for sorbent material. The volume of the interior chamber in a partially assembled column, that is where only one filter assembly is affixed to the column tube, is referred to throughout as the first column sorbent bed volume, "X". In a fully assembled chromatography column of the present invention, both filter assemblies are affixed to their respective ends disposed along the column tube. When affixed, one or more of the filter assemblies protrudes into the interior chamber at a predetermined amount defined by volume "Y", yielding a second column sorbent bed volume "Z", such that Z<X. In this invention, "Y" is a static parameter that does not vary after the column is filled with sorbent and the filter assemblies are securely fixed at both ends. In other words, one or more of the filter assemblies of the instant invention protrude a fixed distance into the column tube. In contrast, columns containing piston-like devices of the prior art have a dynamic "Y" value. Conventional columns of the prior art have filters attached at the column ends with no "Y" value.

The partially assembled column tubes of the present invention have a first column sorbent bed volume (X). This first column sorbent bed volume (X) can be any volume within an appropriate range defined by a particular column. When the column is assembled, defined herein as having both filter assemblies affixed to the two ends of the column tube, the column possess a second column sorbent bed volume (Z) that is always less than the first column sorbent bed volume (X) giving the formula "Z<X". This is due to the compression of the sorbent bed reducing the bed volume by the volume occupied by the protruding filter assembly(s), i.e., volume (Y).

In one embodiment of the present invention, a chromatography column comprises a column tube having a first end and a second end. The column tube has an interior chamber that is a receptacle for sorbent material. In a particular aspect of this embodiment, the first and second ends of the column tube have an inlet and outlet filter assemblies attached thereto, respectively. The inlet filter assembly has a filter housing including a protruding portion and a porous inlet filter. The filter housing has a fluid conduit that is in fluid communication with an inlet fluid connector. Mobile phase enters the chromatography column via this inlet fluid connector and flows into the interior chamber of the column tube via the porous inlet filter. The inlet filter assembly further comprises a column face seal for sealing the column tube under pressure. The inlet filter assembly can be securely affixed to the column tube by means well known to those skilled in the art such as welding, heat sealed, glue, a threaded end fitting or a combination thereof. The inlet filter assembly can optionally have a wiper seal to assist in retaining the sorbent material in the interior chamber as the filter assembly is installed. Alternate versions of this embodiment can utilize the assembly referred to as the inlet filter assembly as the filter assembly on the outlet or at both ends.

In one embodiment of the present invention, a chromatography column comprises a column tube having a first end and a second end, with a recess machined into each end that will receive the filter assembly. A medium collar is installed in each recess to be flush with the interior wall and the end of the tube. The column tube with collar(s) has an interior chamber that is a receptacle for sorbent material. In a particular aspect of this embodiment, the first and second ends of the column tube have an inlet and outlet filter assemblies attached thereto, respectively. The inlet filter assembly has a filter housing with a protruding portion and a porous inlet filter. The inlet filter assembly further compresses the sorbent material as it is being installed. The filter housing has a fluid conduit that is in fluid communication with an inlet fluid connector. Mobile phase enters the chromatography column via this inlet fluid connector and flows into the interior chamber of the column tube via the porous filter. The inlet filter assembly further comprises a column face seal for maintaining the integrity of the interior chamber of the column tube under pressure. The inlet filter assembly can be securely affixed to the column tube by means well known to those skilled in the art such as welding, heat sealed, glue, a threaded end fitting or a combination thereof.

In the present invention, the porous inlet filter can be affixed to the filter housing as one continuous piece, alternatively, the inlet filter can be securely fastened to the filter housing permitting different size inlet filters to be employed using the same basic housing unit. A portion of the porous inlet filter is disposed within the interior chamber of the column tube when affixed to an end of the column tube displacing or compressing bed volume "X" by volume "Y". The extent to which the inlet filter is disposed into the interior of the column tube is predetermined and fixed. Different size inlet filters can be used depending upon the desired depth of penetration into the interior chamber of the column tube. The function of the protruding inlet filter is to mitigate or obviate voids or dead volume occurring within the interior chamber of the column tube caused by, for example, pre-compression of the sorbent bed.

In another embodiment of the present invention, a method for controlling bed density in a chromatography column tube is disclosed. A predetermined amount of sorbent material is added to a partially assembled column tube having a first filter assembly affixed thereto, thus forming a first column sorbent bed volume "X" within the interior chamber of the column tube. The column is then fully assembled by affixing a second filter assembly to the column. The first and second filter assemblies can be affixed to the column using a glue, being welded, threaded, heat sealed or a combination thereof. These are all methods well known to those skilled in the art. The filter assemblies comprise a filter housing and filter. When the column tube is assembled with both filter assemblies, a portion of one or both filter assemblies protrudes into the interior chamber reducing volume "X" by volume "Y" using the protruding filter assembly(ies), thereby forming a second column sorbent bed volume "Z" within the interior chamber of the column tube. The characteristic volume "Y" associated with one or both filter assemblies, and the predetermined amount of sorbent added to the column can be adjusted to achieve a desired bed density within the final column. In a particular aspect of this invention, only one filter assembly has a protruding porous filter.

The column designs and methods for achieving high sorbent bed density as described herein provide the advantage of improving column bed stability as compared to conventional columns which are notorious for instability. A further advantage is the simplicity and inexpensive cost required for fabricating the column of the instant invention. Unlike columns of the prior art in which moving piston or radial compression devices are described, the columns of the present invention have a static system that does not vary over time which establishes a fixed final column volume thus promoting predictable and simplified transfers of chromatographic methods.

BRIEF DESCRIPTION OF THE DRAWINGS

FIG. 1 (*a*)-(*e*) are schematic representations illustrating a column's life span from packing the sorbent bed to running the column and illustrating compression of the column's bed over time;

FIG. 2 (*a*)-(*e*) are schematic representations illustrating the present invention;

FIG. 3 (*a*) is a schematic representation of one embodiment of the present invention, (*b*) is a schematic representation of an inlet filter assembly of the present invention;

DETAILED DESCRIPTION

Figure 4A:
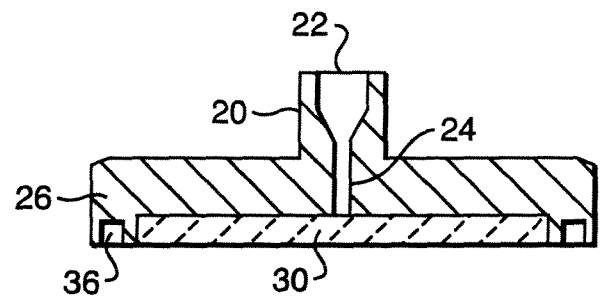
FIG. 4 (*a*) illustrates a conventional filter assembly, (*b*) illustrates one embodiment of the present invention, (*c*) illustrates another embodiment of the instant invention.

The present invention pertains to both apparatus and methods for minimizing column bed compression over time. The invention described herein provides for an improved column design and method for controlling bed density in a chromatography column using one or more protruding filter assemblies. The columns and methods of the present invention produce a higher sorbent bed density than can normally be achieved using a fixed length column of conventional design. This increased sorbent bed density results in improved column stability and extended lifetime.

Liquid Chromatography (hereinafter "LC"), including High Performance Liquid Chromatography (hereinafter "HPLC"), allows for fast, efficient separation and characterization of analytes contained within a given sample. Components of a chromatography system often include pumps that facilitate the movement of an aqueous phase through the system. This aqueous phase (or mobile phase) comprises a solvent that is used to initially equilibrate the chromatography system. The solvent also provides an aqueous milieu for analytes to traverse through the system. Finally, the mobile phase comprises solvent used to elute analytes from a chromatography column.

A vital component of a chromatography system is the chromatography separations column. The column comprises a solid phase (or separation medium) that has sorbent material characterized by a particular chemistry. The solid phase can be a silica-based, polymeric-based or inorganic/organic hybrid composition. There are separations columns used for reverse-phase, normal-phase, anion or cation exchange, size-exclusion and affinity chromatography. The solid phase, in combination with the mobile phase, effectuates differential separation of analytes contained within a sample matrix. The solid phase generally consists of chemical polymers that interact with a certain class of analytes. For example, ion-exchange LC columns have a solid phase chemistry that interacts specifically with analytes that are ionic in nature. To illustrate this principle, anion-exchange columns have a solid phase cationic functional group that will interact, in a non-covalent manner, with anions present in the sample matrix. Depending upon the mobile phase conditions used, certain anions of the sample will be eluted from the column's solid phase, while other anions of the sample will be retained.

Once the analytes are eluted from the column, they traverse into and through a detector. There are a variety of detection systems that can be employed in a chromatography system. For example, there is the ultraviolet/visible absorbance that detects analytes within the UV range. There are other detection systems like infra-red, refractive index, radioactivity, fluorescence, mass spectrometry, evaporative light scattering, and NMR.

The fluidics of any chromatography system requires the presence of tubing that serves as passageways for the mobile phase throughout the entire system. Separation columns are in fluid communication with the mobile phase via this tubing. The tubing connects the column to the system's fluidics via chromatography fittings.

The typical packing and compression of a sorbent bed 12 in a conventional fluid chromatography column 10 is shown in FIG. 1. Sorbent material 12 (also referred to as "solid phase" or "packing material") is extruded from a packing apparatus 14 through an orifice 16 into a receiving column tube 10. See FIG. 1a. The column tube 10 is usually filled under pressure (between approximately 100 to 20,000 psi or even greater) with a desired amount of sorbent material 12, by methods well known in the art. The volume and type of sorbent material 12 is dependent upon the type of chromatography column to be manufactured.

Alternatively, a column tube 10 can be filled with sorbent powder (not shown) under ambient conditions. An aqueous solution can then be introduced into the tube 10 forming a slurry within the column tube 10. As mobile phase traverses through the column, the sorbent bed 12 becomes compressed.

The chromatography column tube 10 has a longitudinal or vertical axis that extends between a first end 11 and a second end 13 of the column tube 10. The longitudinal axis can range from about 1 to about 1000 mm. The diameter of the column tube 10 can range from about 10 nm to about 100 mm.

Packing material 12 is typically loaded into the column 10 via the inlet end, for example, the first end 11. Before the packing material 12 is added to the column 10, the outlet or second end 13 is typically securely affixed to the column 10, by methods known to those skilled in the art, thus precluding the egress of sorbent material from the column. (The first and second ends are arbitrarily being assigned to the inlet and outlet, respectively, for simplicity.) Yet, the second end 13 typically comprises a fluid outlet (not shown) which permits solvent to exit the column 10 but not sorbent material 12, thus the amount of sorbent material should remain constant as the column is used. Upon completion of packing the column 10, a portion of the column's interior chamber becomes occupied with sorbent material 12 forming a first column sorbent bed volume ("X").

Assuming that a packing apparatus 14 is used in the sorbent material 12 loading process, upon the completion of this loading process, the column 10 is removed from the packing apparatus 14 and the sorbent bed 12 decompresses slightly. See FIG. 1b. After the apparatus 14 is removed and the bed 12 decompresses, sorbent material 12 may extend beyond the open first end 11. If this occurs, then the material 12 is removed so that the packing bed 12 rests flush with the first end 11 of the column 10. See FIG. 1c.

Generally, prior to use in a chromatographic system, the first end 11 of the column 10 is capped. FIG. 1d illustrates the application of an inlet filter assembly 20 in this capping procedure. The filter assembly 20 comprises a filter housing 26 and a porous inlet filter 30. The filter assembly 20 of the prior art is constructed such that the inlet filter's 30 surface edge that is disposed toward the sorbent material 12 remains flush with the end of the column 11. Typically, the inlet filter assembly 20 is secured to the column using means known to those skilled in the art, such as welding, or employing a threaded end fitting 28, or alike (see FIG. 3a).

There is usually a vectorial flow relationship between the first 11 and second 13 ends of the column tube 10. Mobile phase from one or more sources of a chromatographic system enter the chromatographic column via the first end 11 and traverses the column 10 existing it via the second end 13. In fact, this flow vector is illustrated on many commercial chromatography columns. Typically there is an arrow on the external surface of the column tube indicating the preferable flow vector. Over a period of time, an exacerbated void or dead volume 18 develops at or near the first end 11 of the column due to further compression of the sorbent material 12 housed within the column tube 10. See FIG. 1e. The void volume 18 typically occurs between a surface of the inlet filter 30 that is disposed toward the packing bed 12 and first end oriented surface of the sorbent bed 12.

Every column possesses a measurable void volume. However, a highly efficient column possesses a de minimus void volume that is measurable but does not negatively affect peak symmetry or column stability. An exacerbated void or dead volume, as depicted by FIG. 1e, can negatively impact the chromatographic performance of a column. For example, the void volume can serve as a mixing chamber within the column. Chromatographic peaks are negatively impacted as the void volume increases, in fact, this observation often serves as being diagnostic of a poor column. Specifically, optimal USP Plates and Tailing parameters deteriorate as the void volume becomes exacerbated. This dead volume can also result in bed instability. Further, the presence of void or dead volume in a column produces stagnant areas that are breeding grounds for microbes. This is particularly true for columns used in the biotechnology industry. These areas can become ensconced with microbial contamination and moreover, these areas are difficult to access in situ for washing the column. Obviously, this type of contamination is undesirable in chromatography.

The prior art discloses chromatography systems that employ a moveable piston-like system for dynamic compression of the sorbent bed thus attempting to minimize void (or dead) volume present within a column. These columns with a movable device contain sorbent material that is allegedly compressed by a piston-like device as the void volume becomes greater. These movable devices are designed to adjust the internal volume of the sorbent bed within a chromatographic column in response to changes in the sorbent bed during use, thereby attempting to minimize the void volume within the column. However, they are typically very complex requiring multiple components and seals. Additionally, these columns with movable devices require that the column itself be significantly larger in order to operate. Further, and perhaps more significant, these columns with movable devices are associated with difficulty in predicting chromatographic performance. As the bed density and/or column volume changes, these changes may affect column performance, thus limiting a practitioner's ability to predict analyte behavior.

Unlike previous attempts to minimize void or dead volume, the present invention as described herein addresses this chromatographic issue by employing a fixed protruding inlet filter assembly for controlling sorbent bed density.

The sorbent bed density contained within a chromatographic column can be expressed a number of ways. The mass of sorbent per unit volume is the most direct measurement. Comparing gram per cubic centimeter values is useful when working with a single type of sorbent particle, but does not allow comparisons between packed beds where the particles have different physical properties such as density, pore volume, or compressibility.

A commonly used approach for studying packed beds of either solid or porous particles is to measure the interstitial fraction within the packed bed, Dullien, F.A.L., Porous Media Fluid Transport and Pore Structure, Academic Press, San Diego, Calif. 1992, the entire teaching of which is incorporated herein by reference. The interstitial fraction describes the ratio of the volume contained between the packed bed particles compared to the entire bed volume. Depending on factors such as the particle shape, particle size distribution, particle compressibility, and packing technique, the degree of randomness and therefore interstitial fraction will vary over a wide range. In general, chromatographic columns will have interstitial fractions ranging between about 0.26 and about 0.42.

For any given packing material, the stability of the packed bed structure against flow induced stresses is improved as the interstitial fraction is decreased. This increased stability is achieved at the expense of bed permeability, which results in higher operating pressures at a given flow rate through the column as the interstitial fraction is decreased.

A number of techniques have been reported for measuring interstitial fraction. Rustamov, I., T. Farcas, F. Ahmed, F. Chan, R. LoBrutto, J. Chromatography A, 913 (2001) 49-63; and Guan-Sajonz, H., G. Guichon, E. Davis, K. Gulakoshi, D. Smith, J. Chromatography A, 773 (1997) 33-51, the entire teachings of which are incorporated herein by reference. Each method involves certain limitations. The total volume of the bed is comprised of the interstitial volume (volume between particles), and the volume of the particles themselves. In the case of porous particles, the particle volume is further comprised of the pore volume within the particles and the skeletal volume that makes up the backbone of the particles.

For the present invention, the total bed volume can be determined by directly measuring the dimensions of the packed bed. The particle skeletal volume is determined by weighing the mass of sorbent and converting to a volume using the sorbent skeletal density as determined by helium pycnometry. The particle pore volume is determined by weighing the mass of sorbent and calculating the particle pore volume using the specific pore volume per gram determined from nitrogen sorptometry. Once the total bed volume, particle skeletal volume, and particle pore volumes are determined, the interstitial volume is calculated and the interstitial fraction is expressed as a ratio of the interstitial volume to the total bed volume. (Interstitial fraction values for the columns in the Example are given in Table 1.)

A significant feature of the present invention is that lower interstitial fractions, and therefore more stable bed structures, will always be achieved with columns of the present invention compared to what would be achieved using columns of conventional design.

FIG. 2 illustrates one embodiment of controlling bed density in a column using the present invention. Steps (a) through (c) are the same in this figure as are shown in FIG. 1. The column tube 10' is packed with a sorbent material 12' appropriate for the column. Once the column 10' is packed, the packing apparatus 14' is removed and the sorbent bed undergoes decompression. (This step assumes that a packing apparatus is used in order to load the column, as mentioned above, however, this is not always the case.) Any excess packing material 12' is then removed from the first end 11' portion of the column tube 10' by methods known to those skilled in the art. See FIG. 2 a-c.

FIGS. 2 (d) and (e) utilize a filter assembly 20' of the present invention. In these two figures, the column tube 10' comprises a sorbent bed 12' that forms a first column sorbent bed volume X. The filter assembly 20' comprises a housing unit 26' and an inlet filter 30'. In this embodiment, the inlet filter 30' has a protruding portion or region 31 that protrudes into the interior chamber of the column tube 10' and compresses volume X of the sorbent material 12'. This protruding portion 31 can extend into the interior chamber from about 1 to about 100 mm. The difference in bed volume before ("X") and after ("Z") the introduction of the inlet filter 30' (having the protruding portion 31) into the column 10' is defined herein as the "Y" or the displaced or compressed volume. As illustrated, in an assembled column (i.e., column tube with an affixed filter assembly at both ends of the column tube) this protruding portion 31 protrudes into the sorbent bed 12' displacing or compressing "Y volume" of sorbent material 12' thus, forming a second column sorbent bed volume Z, wherein:

$$Z<X \qquad (eq. 1)$$

In other words, the second column bed volume Z is less than the first column bed volume X by volume Y, thus:

$$X=Y+Z \qquad (eq. 2)$$

FIG. 3 depicts another embodiment of the present invention. FIG. 3a illustrates a particular aspect of this embodiment. Depicted is a filter assembly 20' of the present invention comprising a filter housing 26', fluid conduit 24, fluid connector 22, and a porous inlet filter 30'. The filter housing 26' has a protruding portion 31 and the porous inlet filter 30' is mounted therein. Together the protruding portion 31 of the filter housing 26' and the porous inlet filter 30' displace sorbent material 12 from the portion of the column 10 occupied by the protruding portion 31. The inlet filter 30' is disposed adjacent to the packing bed 12 within column tube 10. In order to maintain the internal integrity of the column 10, especially when it is operated utilizing high pressure liquid phase, a column seal 36 is employed. The column seal 36 may be a gasket, O-ring or the like and is securely pressed against the end walls of the column 10 when the filter assembly is affixed to the column. An optional a wiper seal 34, disposed between the circumference of the protruding portion 31 and the inner wall of the column, can be also be used to retain sorbent material 12 within the inner chamber as the protruding portion 31 compresses the material. The filter assembly 20' is secured to the column tube 10 using means known to those skilled in the art, such as a threaded end-fitting 28. In this figure, mobile phase from an integrated chromatography system enters the column via the fluid connector 22 that resides at the apex of the filter housing 26'. The solvent continues through the filter assembly 20' and into the packing bed 12 via the inlet filter 30', if high pressure pumps are used, then it is conceivable that the solvent enters the column under relatively high pressure (from about 100 psi to about 20,000 psi or above). In this aspect, the protruding portion 31 of the inlet filter assembly 20' extends longitudinally beyond the horizontal plane of the column face, thus protruding into the sorbent bed 12.

FIG. 3b depicts one embodiment the filter assembly 20". As observed from FIG. 3b, the inlet filter 30', rather than have the filter housing 26", incorporates a thickness so that after mounting in the filter housing 26", the inlet filter 30' extends into the interior chamber forming the protruding portion 31. Thus, the inlet filter 30' protrudes into the packing bed 12, if present within the column tube 10, and displaces and compresses a predetermined amount of sorbent material in the column tube 10. This compression effectuates a desirable higher bed density by further compressing the sorbent bed 12 thus minimizing the potential for a void volume to form during use. In both of these above embodiments, different depth inlet filters 30' or filter housings 26' can be used depending upon how much volume displacement or compression (Y) is desirable in order to effectuate bed compression and minimize potential void formation. For example, depth penetration can be from about 0.5 mm to about 100 mm, or even greater depending upon the sorbent material 12 and its disposition within the column tube 10 (i.e., the first column bed volume X). A preferred penetration has been found to be between 1.0 and 10 mm. Preferably, the protruding portion 31, either filter housing and filter 20' or filter alone 20" interacts with the sorbent bed 12 moving the upper boundary of the bed a distance equal to the depth of the protruding portion 31 into the interior chamber. Therefore, the first column bed volume X, the packing density achieved during loading and the desired final density are determinative of the length of the protruding portion 31 of the filter assembly 20' required to compress the sorbent bed 12 to form a more compressed (higher density) second column bed having a volume Z.

The inlet filter 30' can be a component that is mounted in the filter housing 26". The inlet filter 30' can be affixed to the filter housing 26" by any means known by those skilled in the art such as snap-fit (or pressure-fit). Alternatively, the inlet filter 30' can be manufactured as a component of the filter housing 26" being structurally continuous with the housing 26".

FIGS. 4 (a) through (c) compare a conventional filter assembly 20 with different embodiments of the present invention. As depicted in FIG. 4a, the conventional filter assembly 20 comprises a filter housing 26, a face seal 36, and inlet filter 30. In this conventional filter assembly 20, the inlet filter's surface adjacent to the packing bed (not shown in FIG. 4, but may be viewed in FIG. 1) rests flush with the column's end face following column assembly. When the conventional filter housing is secured to the column sufficiently tightly that face seal 36 seals the column to the desired pressure rating, there is no protrusion of the inlet filter 30 beyond the first end 11 of the column.

Figure 4B:
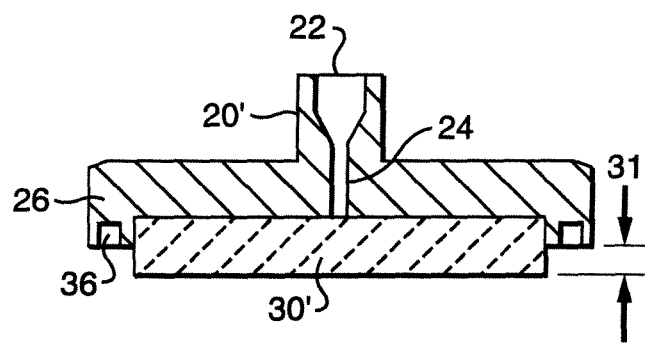

The filter assembly 20' of FIG. 4b is in contrast to the conventional filter assembly 20 of FIG. 4a. The assembly of FIG. 4b depicts one embodiment of the present invention. Here the inlet filter 30' protrudes from the filter housing 26 forming the protruding portion 31. This protruding portion inserts into the interior chamber of a column tube 10 (not shown). The inlet filter's 30' surface adjacent to the packing bed extends beyond the horizontal plane of the column face. When the filter assembly 20' is sufficiently sealed to the column 10 by face seal 36, the inlet filter 30' is fully inserted in the column tube 10. The depth of the protruding portion 31 can vary depending upon the additional compression desired, for example, from about 1 mm to about 100 mm, or greater. The radial width of the inlet filter 30' can vary but should be a friction fit in the column tube 10. It is preferably equal to the internal width of the column tube for best performance and consistent packing. The radial width of the inlet filter 30' is less than that of the filter housing 26', as shown in FIG. 4 in order to allow the filter housing 26' to rest on the column walls and seal column assembly.

Figure 4C:
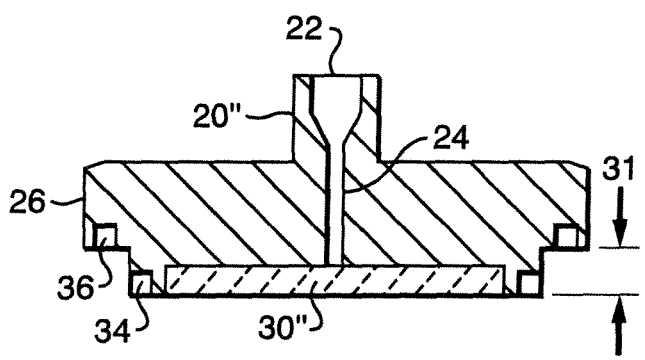

The filter assembly 20" of FIG. 4c illustrates yet another embodiment of the instant invention. In this embodiment, the filter housing 26" is extended axially toward the packing bed (not shown) forming a protruding portion 31. The protruding portion 31 of the filter housing 26" that extends into the packing bed holds a inlet filter 30" having a standard depth. The rim of the filter housing 26" around the inlet filter 20" provides rigidity and strength to enable greater compression to be achieved. In a particular aspect of this embodiment, a wiper seal 34 is employed to assure that the sorbent material remains in the interior chamber creating a uniformly packed column. The wiper seal 34 is annularly disposed about the exterior of the filter housing 26 and preferably is comprised of rubber, polyurethane, polyetheretherketon (PEEK™), plastic, polyethylene, Teflon®, nylon and alike. The filter housing 26" and wiper seal 34 together have a diameter that is equal to or slightly greater than the internal diameter of the column tube to allow the wiper seal 34 to be compressed, sweeping the sorbent material into the internal chamber as the protruding portion 31 is inserted. While the wiper seal 34 is compressed sufficiently to retain the sorbent material during assembly, the column seal 36 is required to seal the column tube at operational pressures. The protruding portion (31) of the filter housing 26" penetrating into the packing bed can be from about 1 mm to about 100 mm, or greater.

Figure 5A:
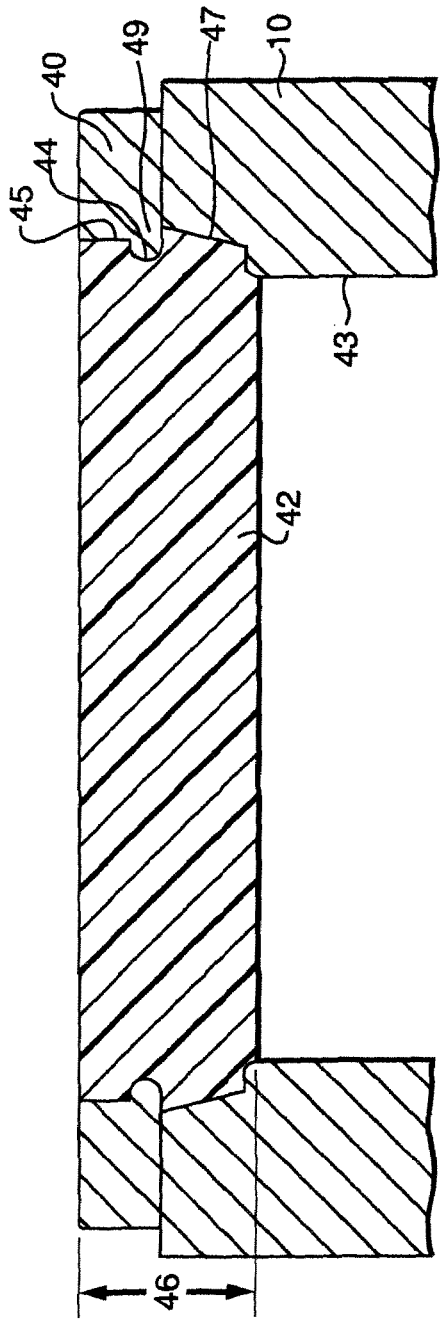
FIG. 5 (*a*) illustrates a column with a medium collar installed and (*b*) illustrates an embodiment of a filter assembly for this column according to the invention.
Figure 6A:
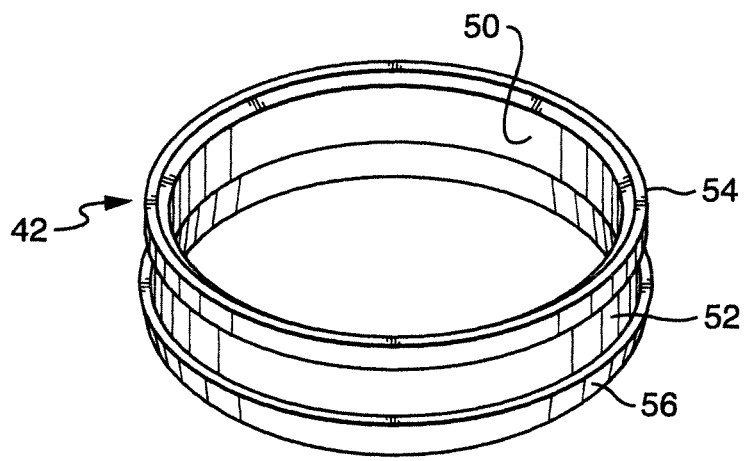
FIG. 6 (*a*) illustrates a medium collar and (*b*) illustrates a cross section of a medium collar.
Figure 6B:
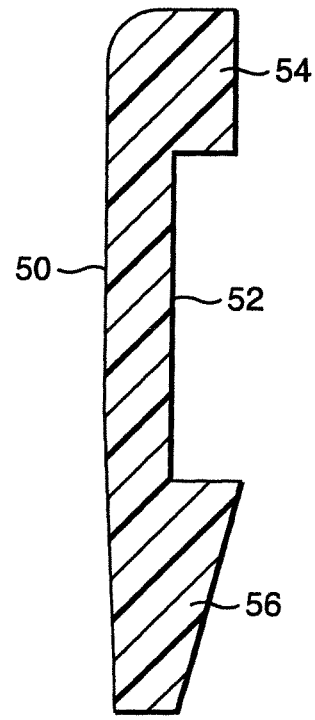
Figure 7:
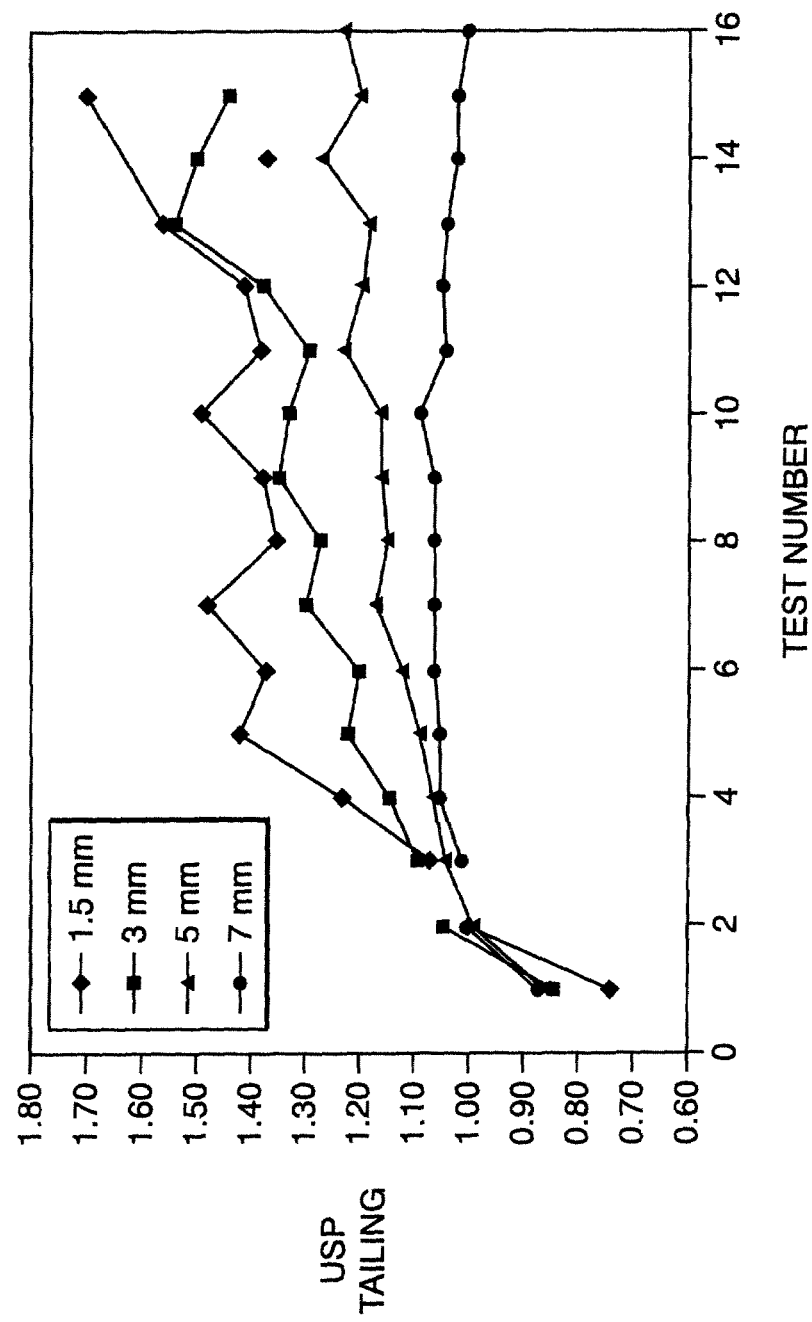
FIG. 7 illustrates experimental data measuring USP Trailing Factor vs Column Test under normal flow conditions using a 50×100 mm column.

A further embodiment of the controlled density column is implemented with a modified column tube as illustrated in FIG. 5A. This embodiment utilizes a matched set of column and filter assembly(s) to be used with that column. At each end that will be used to compress the sorbent material, a recess 44 is cut in the inner wall 43 of the column tube 40. This recess has a length 46 equal to the depth of the protruding portion 31' of the filter assembly 20'" to be used to with the column. The recess is shaped to receive a medium collar 42. The medium collar 42, as shown in detail in FIG. 6, has a smooth interior wall with a slightly curved leading edge, a top rib 54 and a bottom rib 56 that bracket a stabilizing recess 52. The recess 44 has a top indent 45 to receive the top rib 54, a bottom indent 47 to receive the bottom rib 56 and a locking rib 49 to fit in the stabilizing recess 52. The medium collar 42 and recess 44 are matched so that an essentially smooth inner wall 43 is produced when the medium collar 42 is installed in the recess 44 and the medium collar 42 and end of the column tube 40 are aligned.

Figure 5B:
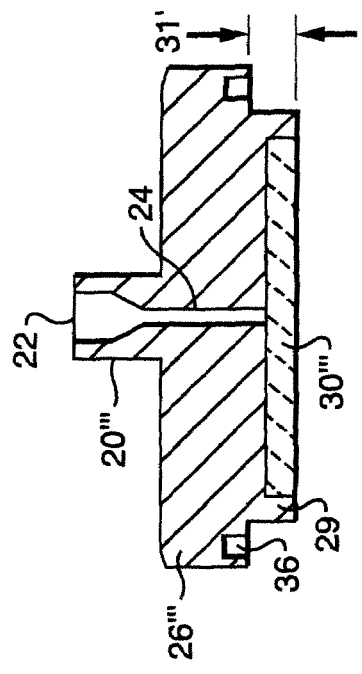

The filter assembly 20''' shown in FIG. 5b is used with this column. The filter assembly 20''' comprises a filter housing 26''' having a protruding portion 31' that has a depth that is equal to the height of the recess 42 and medium collar 44. The filter housing 26''' is sized so that the top end incorporates a groove for the end seal 36 and spans the thickness of the column tube. The protruding portion 31' is sized with a diameter that matches the inner diameter of the column tube. The thickness of the rim 29 of the filter housing 26''' is selected to provide sufficient strength for the insertion process while allowing the maximum diameter for the inlet filter 30'''. When the filter assembly 20''' is used with this column, the outer surface of the protruding portion 31' and inner surface 50 of the medium collar 42 make sweeping contact as the filter assembly is inserted and prevent any sorbent from remaining in the space between the column and the protruding portion 31'.

In manufacturing columns with this embodiment, column tubes 10 are first processed to incorporate a recess 44 in one or both ends. The medium collars 42 are manufactured of a sufficiently flexible material that they may be flexed and snapped into the recess(es). Once the medium collar 42 is installed in the column tube, the filling and manufacturing process proceeds as previously described.

Materials suitable for constructing the inventive columns include, but are not limited to, stainless steel, Teflon, metals, plastics, glass, polyurethane, polyethylene, nylon, and alike. Preferred materials for standard sized columns are stainless steel, with Teflon the preferred material for the medium collar and/or wiper seal. Preferred materials for

EXAMPLE

The following example is intended to illustrate an embodiment of the present invention and should not be viewed as limiting the scope of the instant invention in any manner.

A series of columns are packed having 50 mm internal diameter and 100 mm initial length. Each column has an inlet filter/end fitting as described in FIG. 3 where the inlet filter extends inside the length of the column at distances of 1.5 mm, 3 mm, 5 mm, and 7 mm. Columns are packed with Waters' 5 µm, Xterra Prep MS C18 sorbent by preparing a slurry containing 140 g sorbent in 1550 mL of a toluene/cyclohexanol mixture (50/50 by volume), and pumping the slurry into the column at a pressure of 6000 psi. Once packed, excess sorbent is scraped flush with column face, and the inlet filter/end fitting is inserted into the column end and sealed in place with the threaded column end fitting.

Each column is tested for peak shape and efficiency by HPLC using a mobile phase consisting of a 50/50 acetonitrile/water (by volume) at a flow rate of 125 mL/minute, and injecting 500 µL of a sample mixture comprising 8 µL/mL acetone (unretained peak) and 1.2 mg/mL acenaphthene (retained peak) dissolved in mobile phase. The columns are measured for efficiency using the standard USP Tangent Efficiency Method, and for peak shape using the standard USP Tailing Method, Uwe D. Neue, HPLC Columns; Theory, Technology, and Practice, Wiley, New York, N.Y. 1997, the entire teaching of which is incorporated herein by reference. Columns were monitored over several days and multiple injections to determine performance stability. At the conclusion of testing, each column was emptied, and the weight of sorbent material was determined after drying the sorbent at 70° C. under 29"Hg vacuum. The final sorbent weight was divided by the column volume for each column to determine the actual bed density (g/cc) for each column. Interstitial fractions for each column were calculated using the previously described method. Table 1 shows a comparison of interstitial fraction for each column. A value for a column having no protrusion (conventional design column) was calculated from an extrapolated column volume and sorbent mass.

TABLE 1

| Protrusion (mm) | Measured Bed Volume cm³ | Measured Bed Density g/cm³ | Interstitial Fraction |
|---|---|---|---|
| 0 | 196.34 | 0.6214 | 0.342 |
| 1.5 | 193.40 | 0.6308 | 0.332 |
| 3 | 191.24 | 0.6380 | 0.324 |
| 5 | 186.97 | 0.6520 | 0.310 |
| 7 | 183.29 | 0.6680 | 0.293 |

Measured sorbent pore volume using nitrogen sorptometry = 0.43 cc/g
Measured sorbent skeletal density using helium pycnometry = 1.59 g/cc FIG. 5 shows the change in USP peak tailing for each column with successive column tests. Results for the initial test typically gives poor results due to column equilibration issues, and can be ignored. The results in FIG. 5 indicate that columns packed at higher bed density using longer inlet filter extensions provide superior USP tailing results, and better column stability than columns packed at lower bed density.

Table 2 below summarizes the change in USP Tailing and USP efficiency for each packed column.

TABLE 2

| Column Efficiency USP Tangent Protrusion Length | | | | | USP Tailing Protrusion Length | | | | |
|---|---|---|---|---|---|---|---|---|---|
| Test # | 1.5 mm | 3 mm | 5 mm | 7 mm | Test # | 1.5 mm | 3 mm | 5 mm | 7 mm |
| 01 | 1284 | 3542 | 3233 | 4941 | 01 | 0.74 | 0.84 | 0.86 | 0.87 |
| 02 | 6907 | 7404 | 4943 | 6363 | 02 | 1.0 | 1.04 | 0.99 | 1.0 |
| 03 | 7403 | 7691 | 6253 | 6889 | 03 | 1.07 | 1.09 | 1.04 | 1.01 |
| 04 | 6943 | 7593 | 6357 | 7793 | 04 | 1.23 | 1.14 | 1.06 | 1.05 |
| 05 | 6832 | 7360 | 6513 | 8132 | 05 | 1.42 | 1.22 | 1.09 | 1.05 |
| 06 | 6874 | 7519 | 6608 | 7965 | 06 | 1.37 | 1.2 | 1.12 | 1.06 |
| 07 | 6798 | 7186 | 6443 | 7881 | 07 | 1.48 | 1.3 | 1.17 | 1.06 |
| 08 | 6935 | 7272 | 6567 | 7369 | 08 | 1.35 | 1.27 | 1.15 | 1.06 |
| 09 | 6924 | 7008 | 6522 | 8090 | 09 | 1.38 | 1.35 | 1.16 | 1.06 |
| 10 | 6843 | 7043 | 6627 | 8086 | 10 | 1.49 | 1.33 | 1.16 | 1.09 |
| 11 | 6767 | 7212 | 6447 | 8008 | 11 | 1.38 | 1.29 | 1.23 | 1.04 |
| 12 | 6670 | 7077 | 6600 | 7927 | 12 | 1.41 | 1.38 | 1.2 | 1.05 |
| 13 | 6571 | 6330 | 6626 | 7860 | 13 | 1.56 | 1.54 | 1.18 | 1.04 |
| 14 | 6821 | 6570 | 6579 | 7808 | 14 | 1.37 | 1.5 | 1.27 | 1.02 |
| 15 | 6557 | 6917 | 6516 | 7784 | 15 | 1.7 | 1.44 | 1.2 | 1.02 |

What is claimed is:

1. A method of constructing a chromatography column, comprising:
   providing a column tube, wherein said column tube has a first end, a second end, an interior wall and an exterior wall, wherein said tube has a tube chamber and wherein said tube has a recess machined in said first end;
   securing a medium collar having a top end, a bottom end, a substantially smooth inner surface, and an articulated external surface in said recess with said external surface abutting said recess, said inner surface substantially aligned with said interior wall and said top end aligned with said first end, wherein said tube with said medium collar installed has an interior chamber;
   affixing an outlet filter assembly to said second end of said column tube, wherein said outlet filter assembly has a second housing for mounting to said second end and a fluid outlet that is in fluid communication with said housing, wherein a first column sorbent bed volume is defined by said interior chamber and said affixed outlet filter assembly;

adding a separation medium into said interior chamber of said column tube;

inserting an inlet filter assembly onto said first end, said inlet filter assembly having a first housing for mounting to said first end, a fluid inlet that is in fluid communication with said first housing, and end seal fitted to said first housing for mating with said tube first end, and a protruding portion that extends from said first housing into said interior chamber, said protruding portion cooperating with said medium collar to retain said separation medium in said chamber; and affixing said inserted inlet filter assembly to said first end, wherein a second column sorbent bed volume is defined by said tube affixed to said outlet filter assembly and said inlet filter assembly, and wherein said second bed volume is less than said first bed volume.

2. The method of claim 1 wherein said adding operation is followed by packing said separation medium in said interior chamber.

3. The method of claim 1 wherein said adding operation is followed by passing a fluid through said separation medium to compress said medium.

4. The method of claim 1 wherein pressure is applied to said inlet filter assembly to effect said insertion.

* * * * *